US010364283B2

(12) United States Patent
Oesser et al.

(10) Patent No.: US 10,364,283 B2
(45) Date of Patent: *Jul. 30, 2019

(54) COLLAGEN HYDROLYSATE AND USE THEREOF

(71) Applicant: GELITA AG, Eberbach (DE)

(72) Inventors: Steffen Oesser, Glücksburg (DE); Monika Giesen-Wiese, Höchst (DE); Hans-Ulrich Frech, Weinheim (DE); Stephan Hausmanns, Heidelberg (DE)

(73) Assignee: GELITA AG, Eberbach (DE)

( * ) Notice: Subject to any disclaimer, the term of this patent is extended or adjusted under 35 U.S.C. 154(b) by 279 days.

This patent is subject to a terminal disclaimer.

(21) Appl. No.: 14/697,759

(22) Filed: Apr. 28, 2015

(65) Prior Publication Data
US 2015/0232534 A1 Aug. 20, 2015

Related U.S. Application Data

(63) Continuation of application No. PCT/EP2013/072894, filed on Nov. 4, 2013.

(30) Foreign Application Priority Data

Nov. 6, 2012 (DE) ................. 10 2012 110 612

(51) Int. Cl.
  C07K 14/78 (2006.01)
  A61K 8/65 (2006.01)
  A61K 38/01 (2006.01)
  A61K 35/32 (2015.01)
  A61K 45/06 (2006.01)
  A23J 3/34 (2006.01)
  A23L 33/18 (2016.01)
  A61K 38/00 (2006.01)

(52) U.S. Cl.
  CPC .............. *C07K 14/78* (2013.01); *A23J 3/342* (2013.01); *A23L 33/18* (2016.08); *A61K 35/32* (2013.01); *A61K 38/014* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,120,761 A * | 6/1992 | Finnan | A23J 3/342 424/499 |
| 5,760,094 A * | 6/1998 | Alexander | A61K 9/2063 424/465 |
| 5,948,766 A | 9/1999 | Milan et al. | |
| 7,495,076 B2 | 2/2009 | Gu et al. | |
| 2004/0053207 A1* | 3/2004 | Griffiths | A01N 1/02 435/2 |
| 2006/0269987 A1 | 11/2006 | Dolphin et al. | |
| 2011/0124570 A1 | 5/2011 | Drieu La Rochelle et al. | |
| 2011/0158949 A1* | 6/2011 | Thurlby | A23L 33/135 424/93.4 |
| 2012/0128737 A1 | 5/2012 | Oesser | |
| 2012/0142598 A1* | 6/2012 | Pam | A23G 3/44 514/17.2 |
| 2012/0330434 A1* | 12/2012 | Ding | A61F 2/28 623/23.52 |
| 2013/0252899 A1 | 9/2013 | Hausmanns et al. | |
| 2013/0345139 A1 | 12/2013 | Oesser et al. | |

FOREIGN PATENT DOCUMENTS

| | | | |
|---|---|---|---|
| CN | 102094056 A | 6/2011 | |
| DE | 10 2010 060 564 A1 | 5/2012 | |
| DE | 10 2011 000 997 A1 | 9/2012 | |
| EP | 0 682 873 A1 | 11/1995 | |
| EP | 0 777 491 B1 | 6/1997 | |
| EP | 0 798 001 B1 | 1/2004 | |
| EP | 2 088 157 A1 | 8/2009 | |
| JP | 2008-247809 A | 10/2008 | |
| WO | WO 2006128685 A2 * | 12/2006 | ............ C08H 1/06 |
| WO | WO 2009/101146 A1 | 8/2009 | |
| WO | WO 2010/149596 A1 | 12/2010 | |
| WO | WO 2011/072596 A1 | 6/2011 | |

OTHER PUBLICATIONS

Reference (1999) Define the following terms: monomer, polymer, weight-average molecular weight and number-average molecular weight, pp. 1-3.*
Abrams, S., et al., "A combination of prebiotic short- and long-chain inulin-type fructans enhances calcium absorption and bone mineralization in young adolescents", Am J Clin Nutr, 82, pp. 471-476 (2005).
Dybka, K., et al., "Collagen hydrolysates as a new diet supplement", Food Chemistry and Biotechnology, 73, pp. 83-92 (2009).
Heyns, K., et al., "Die hydrolyse synthetischer und natürlicher substrate durch kollagenase aus clostridium histolyticum", Über Proteine und deren Abbauprodukte, 321, pp. 184-200 (1960).
Schrieber, R., et al., *Gelatine Handbook*, Wiley-VCH Verlag GmbH (2007) contents; pp. 45-131.

(Continued)

Primary Examiner — Manjunath N Rao
Assistant Examiner — Samuel W Liu
(74) Attorney, Agent, or Firm — Leydig, Voit & Mayer

(57) ABSTRACT

The present invention relates to a collagen hydrolysate which is produced by enzymatic hydrolysis of type-B bone gelatin, wherein the collagen hydrolysate is formed from peptides of which at least 50% by weight, in particular at least 70% by weight have a molecular weight of 1,500 Da to 3,500 Da, and which have a mean molecular weight in the range from 4,000 Da to 8,000 Da, in particular in the range from 4,500 Da to 6,000 Da. The invention also relates to the use of this collagen hydrolysate as an active ingredient to maintain and/or improve the health of the bones, in particular to prevent and/or treat osteoporosis. The invention further relates to a nutritional supplement which comprises the collagen hydrolysate.

13 Claims, 2 Drawing Sheets

(56) References Cited

OTHER PUBLICATIONS

Figure 1:
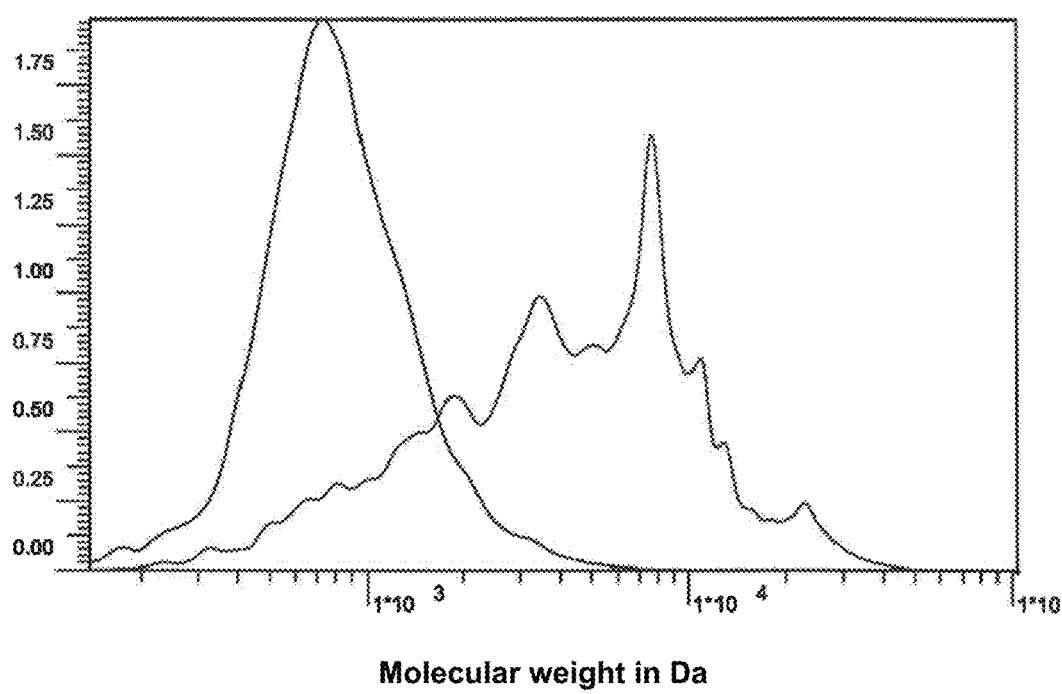

Kumar, J. Suresh, et al., "Gelatin and its applications", *44th Leather Research Industry Get-Together*, Jan. 29-30, 2010 (26 pages).
Zague, V., "A new view concerning the effects of collagen hydrolysate intake on skin properties", *Arch Dermatol Res*, 300, pp. 479-483 (2008).
Gómez-Guillén, M.C. et al., "Functional and bioactive properties of collagen and gelatin from alternative sources: A review", *Food Hydrocolloids*, 25, pp. 1813-1827 (2011).
Oesser, S. et al., "Stimulation of type II collagen biosynthesis and secretion in bovine chondrocytes cultures with degraded collagen", *Cell Tissue Res*, pp. 311, 393-399 (2003).
International Search Report, PCT/EP2013/072894, dated Feb. 4, 2014.
International Preliminary Report on Patentability, PCT/EP2013/072894.
AOMB IP Consultants, Third Party Observations for European Patent Application No. EP20130789518, submitted Jun. 23, 2016.
Moskowitz, "Role of Collagen Hydrolysate in Bone and Joint Disease," *Seminars in Arthritis and Rheumatism*, 30(2):87-99 (2000).

\* cited by examiner

Molecular weight in Da

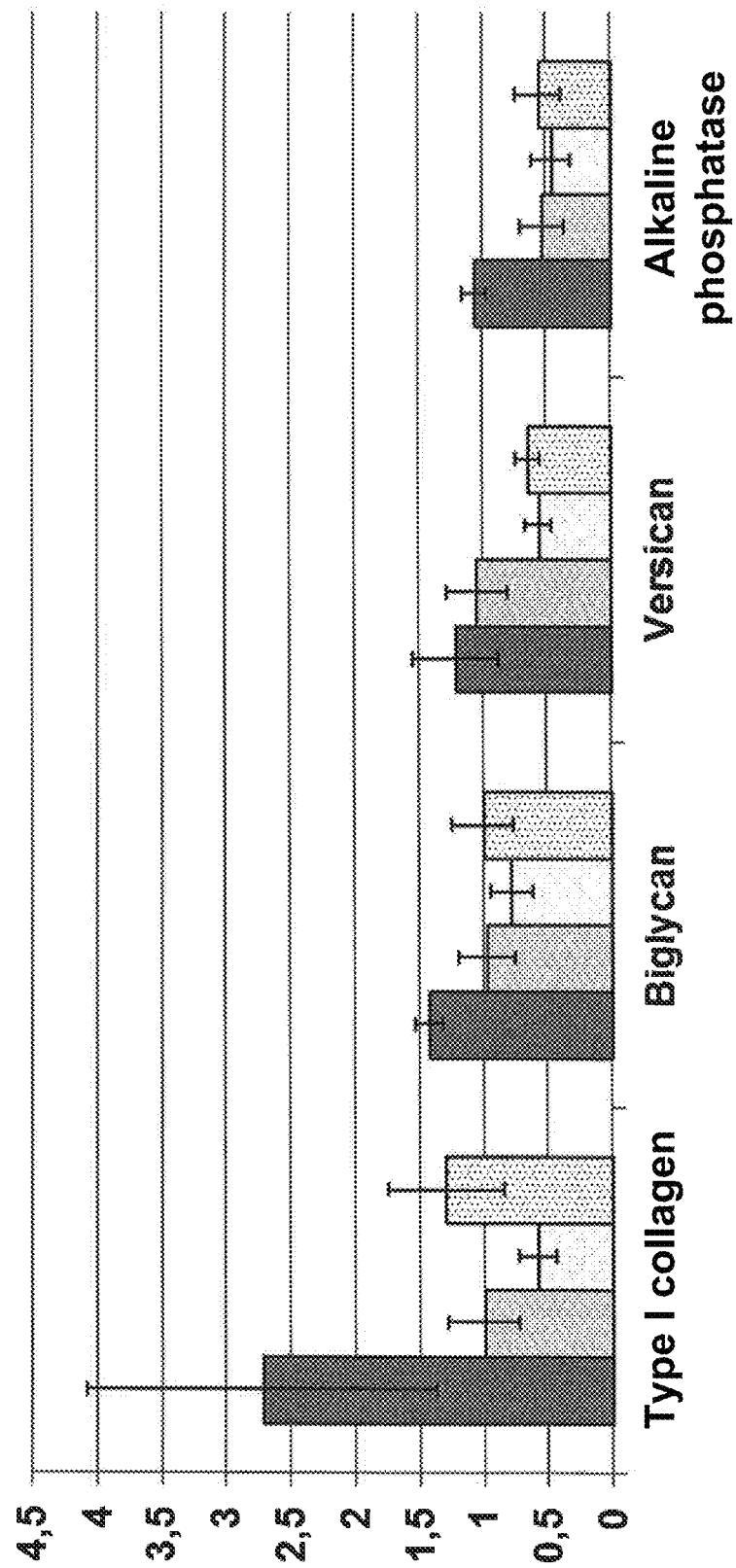

COLLAGEN HYDROLYSATE AND USE THEREOF

CROSS REFERENCE TO RELATED APPLICATIONS

This application is a continuation of PCT/EP2013/072894, filed on Nov. 4, 2013, which claims the benefit of German Patent Application 10 2012 110 612.6 filed on Nov. 6, 2012, each of which is incorporated by reference.

BACKGROUND OF THE INVENTION

The present invention relates to a novel collagen hydrolysate.

The invention also relates to the use of this novel collagen hydrolysate as an active ingredient to maintain and/or improve the health of the bones, in particular to prevent and/or treat osteoporosis. The invention further relates to a nutritional supplement which comprises the collagen hydrolysate.

The bones of vertebrates and therefore also of humans owe their great strength and mechanical stability to the special structure of the bone matrix which is synthesised by the osteoblasts (bone cells). The two essential components of the bone matrix are, firstly, a framework of cross-linked collagen, wherein particularly in the case of the bone matrix, this is type I collagen. The cross-linking thereof takes place essentially by means of the amino acids lysine and hydroxylysine. The second component is hydroxylapatite (also known as apatite-(CaOH)) which is embedded in the bone matrix (mineralisation of the bones). This structure of the bone is roughly comparable to that of steel-reinforced concrete wherein the properties of the steel framework (corresponding to the collagen) and of the concrete (corresponding to the hydroxylapatite) also complement one another while forming an extremely stable structure.

In contrast to many other tissue types, bone has a relatively high regeneration capability, that is, the extracellular bone matrix is continuously built up and broken down again. When a disturbance of this equilibrium comes about, that is, an insufficient building up of new bone matrix, bone loss occurs. This loss of bone density is known as osteoporosis and can have a variety of causes. Typically, osteoporosis occurs with increasing age (mostly from the start of the fifth decade of life), particularly frequently in women following the menopause (postmenopausal osteoporosis).

It has been known for some time that the loss of bone density in osteoporosis can be counteracted by oral administration of collagen hydrolysates. Collagen hydrolysates, which are obtained by the enzymatic hydrolysis of animal collagen contain a mixture of peptides with different chain lengths and molecular weights. The European patent EP 0 777 491 B1 discloses, for example, the use of a collagen hydrolysate with a mean molecular weight of 1,000 Da to 40,000 Da, which is produced by enzymatic hydrolysis of skin collagen, for the treatment of postmenopausal osteoporosis. It is assumed that this advantageous effect of collagen hydrolysate on the health of the bones is based on the stimulation of the biosynthesis of type I collagen and other matrix proteins by the osteoblasts, as has similarly been previously demonstrated in vitro for chondrocytes (see S. Oesser and J. Seiffert (2003), *Cell Tissue Research* (311) 393-399).

BRIEF SUMMARY OF THE INVENTION

Various collagen hydrolysates differ with regard to the molecular weight distribution of the peptides they contain, their amino acid sequence and other parameters, depending on the starting material and the production method. It is an object of the present invention to propose a collagen hydrolysate which has particularly good effectiveness with regard to the maintenance and/or improvement of the health of the bones.

This object is achieved according to the invention with a collagen hydrolysate which is produced by enzymatic hydrolysis of type-B bone gelatin, wherein the collagen hydrolysate is formed from peptides of which at least 50% by weight have a molecular weight of 1,500 Da to 13,500 Da, and which have a mean molecular weight in the range from 4,000 Da to 8,000 Da.

DETAILED DESCRIPTION OF THE INVENTION

Investigations carried out by the inventors on the stimulation of the synthesis of matrix proteins by osteoblasts in vitro, which are described in greater detail below, have surprisingly shown that a collagen hydrolysate of this type has a significantly greater stimulating effect as compared with different other hydrolysates, particularly on the synthesis of type I collagen. A collagen hydrolysate in which at least 70% by weight of the peptides have a molecular weight of 1,500 Da to 13,500 Da, and/or which have a mean molecular weight in the range from 4,500 to 6,000 Da, has proved to be particularly advantageous.

Of particular interest in this result is the high effectiveness of a collagen hydrolysate specifically made from bone gelatin, especially since from the prior art, the use rather of hydrolysates from collagen or gelatin from animal skin (mostly from pig skin, but also from fish skins) is known. In general, gelatin as a denatured soluble form of collagen is a very suitable starting material for enzymatic hydrolysis. The bone gelatin used in the context of the invention as the starting product for the hydrolysate is a type-B gelatin, which is preferably produced by alkaline breakdown of collagen from bones of vertebrates, particularly from ossein. Ossein involves degreased and demineralised bones. Favourably, ossein from cattle bones is used.

The isoelectric point (IEP) of the bone gelatin used as the starting material is preferably below 5.5. By contrast therewith, type-A gelatins which are produced by acidic decomposition of the collagen have an isoelectric point of above 7.

In the collagen hydrolysate according to the invention, the peptides preferably have an overall amidation level of the glutamine groups and/or glutamic acid groups and of the asparagine groups and/or aspartic acid groups of less than 15%, particularly less than 10%. The amidation level is thus calculated by dividing the molar proportion of the glutamine and asparagine groups by the molar proportion of the glutamine, glutamic acid, asparagine and aspartic acid groups in the peptides. The latter value is given by the natural amino acid composition of the collagen and typically amounts to approximately 1.12 mmol/g. The molar proportion of the glutamine and asparagine groups can be determined by acid hydrolysis of the amides and determination of the ammonia formed therefrom. A low amidation level of the peptides can be achieved, particularly, through the alkaline breakdown of the (type-B) gelatin used.

Interestingly, the investigations on the simulation of the matrix protein synthesis by osteoblasts have also shown that the collagen hydrolysate according to the invention with a preferred mean molecular weight of 4,600 Da to 6,000 Da has a greater effectiveness than various low-molecular hydrolysates. The viscosity of the collagen hydrolysate also correlates to the molecular weight of the peptides obtained. In this regard, it is preferable if a 20% by weight aqueous solution of the collagen hydrolysate has a viscosity at 25° C. of more than 5 mPa·s, in particular more than 6 mPa·s.

The collagen hydrolysate according to the invention preferably has an ammonium, sulphate and phosphate content of less than 300 ppm each, in particular less than 100 ppm. Correspondingly low salt contents can be maintained already in the production of the bone gelatin used for the hydrolysis.

For the enzymatic production of collagen hydrolysate, different proteases, particularly of microbial origin, can be used, wherein their different specificities for particular amino acids directly influence the molecular structure of the resulting peptides and thus also their effectiveness. It has been found that with regard to the simulation of the osteoblasts, a particularly effective collagen hydrolysate can preferably be produced by hydrolysis of the gelatin with a neutral endoprotease from *Bacillus subtilis*.

According to a preferred embodiment of the invention, the collagen hydrolysate is produced through the action of the endoprotease at a temperature of 40° C. to 60° C., particularly approximately 50° C., over a period of 20 min to 40 min, particularly approximately 30 min.

Aside from the above-described collagen hydrolysate as such, the present invention also relates particularly to its use as an active ingredient to maintain and/or improve the health of the bones, in particular to prevent and/or treat osteoporosis. Due to the marked stimulating effect of the collagen hydrolysate according to the invention on the synthesis of matrix proteins by the osteoblasts, which can be demonstrated by in vitro experiments, a disruption of the equilibrium between bone formation and degradation can be specifically counteracted through oral administration of the collagen hydrolysate.

An essential aspect of the invention concerns the use of the collagen hydrolysate as an active ingredient to prevent and/or treat postmenopausal osteoporosis. According to estimates, approximately 50% of women aged over 50 are affected by this type of bone loss and, in the first five years after menopause, up to 20% of the bone substance can be lost.

The present invention therefore relates to a method for preventing and/or treating osteoporosis, particularly postmenopausal osteoporosis, wherein the method comprises the oral administration to a patient of the collagen hydrolysate according to the invention, particularly to a female patient over 50 years of age.

Since for hydrolysates from animal or plant proteins, approval as a pharmaceutical product is not required, the collagen hydrolysate according to the invention can favourably be formulated as a nutritional supplement. The collagen hydrolysate can be present in the form, for example, of a powder, a granulate, a solution or a suspension or in the form of tablets, capsules, caplets or sachets, if appropriate, in combination with suitable additives or inactive ingredients. Alternatively, the collagen hydrolysate can also be added directly to a food product.

The daily oral intake is preferably in the range from 1 g to 15 g of the collagen hydrolysate, preferably from 2 g to 10 g, more preferably from 2 g to 7 g, and particularly preferably in the range from 2.5 g to 5 g. The relevant quantity can favourably be formulated as a single daily dose.

A further preferred embodiment of the invention relates to a nutritional supplement which, aside from the collagen hydrolysate according to the invention, comprises one or more prebiotics. The combination of collagen hydrolysate with one or more prebiotics is based on the consideration that for a particularly effective regeneration of the bone substance, not only the biosynthesis of collagen and other matrix proteins, but also the formation and incorporation of hydroxylapatite in a sufficient quantity must be enabled. A limiting factor herein is the supply to the bone matrix of calcium, although the sufficient intake of calcium with the nutrition is not the problem (with a balanced diet, this is generally guaranteed), but rather the sufficient resorption of the absorbed calcium in the gut which is limited, particularly due to the formation of barely soluble calcium salts.

It has been found that the resorption of calcium and thus the mineralisation of the bones can be improved by the administration of prebiotics. Prebiotics are generally non-digestible food constituents which stimulate the growth and/or activity of particular microorganisms of the gut flora and thereby have a positive effect on the health. Although the exact mechanism by means of which this effect of the prebiotics advantageously influences the calcium resorption has not yet been entirely explained, the above-described positive effect has been shown, for example, for the administration of fructans to children from about 12 years of age (see S. Abrams et al. (2005), *American Journal of Clinical Nutrition* (82) 471-476).

Thus, through the joint administration of collagen hydrolysate and prebiotics, the formation of the two essential constituents of the bone matrix is stimulated and thereby a synergistic effect is achieved with regard to the health of the bones, particularly in respect of the prevention and/or treatment of osteoporosis.

The nutritional supplement according to the invention can in principle comprise any weight ratio of collagen hydrolysate and prebiotic or prebiotics. In order to ensure a sufficient supply with both components, however, it is preferable if the proportion of the collagen hydrolysate and of the prebiotic or prebiotics each amount to approximately 20% to approximately 80% by weight, and more preferably approximately 40% to approximately 60% by weight. The nutritional supplement can comprise, in particular, a mixture of the two constituents in a weight ratio of approximately 1:1.

The prebiotic or prebiotics used in the nutritional supplement according to the invention is/are preferably selected from the oligosaccharides and/or polysaccharides. Oligosaccharides and polysaccharides constitute the majority of the known prebiotically active substances wherein, through the use of such substances, the additional advantageous effect comes about that the taste of the nutritional supplement is significantly improved in comparison to pure collagen hydrolysate. Although collagen hydrolysates which are typically described as flavour-neutral can be produced by corresponding methods, many users perceive an adverse taste effect described as "glutinous". Surprisingly, the negative taste components of collagen hydrolysate can be almost completely eliminated by the combination with prebiotic oligosaccharides and/or polysaccharides.

The prebiotic or prebiotics is/are preferably selected from inulin, fructans, galacto-oligosaccharides (GOS), fructo-oligosaccharides (FOS), resistant maltodextrins, polydextrose and mixtures thereof. These comprise both naturally occurring and synthetically produced polysaccharides. Inulin is a fructan which comprises up to 100 fructose units and an independent glucose unit. Fructo-oligosaccharides and galacto-oligosaccharides exclusively comprise fructose or galactose units (typically up to 10), and polydextrose comprises a synthetic polysaccharide made of glucose, sorbitol and citric acid units.

It is further preferred if the nutritional supplement comprises, as a further component, at least one soluble calcium salt. By this means, at the same time, a sufficient supply to the user of calcium is ensured, regardless of his/her other nutritional habits.

In principle, this can involve all the soluble calcium salts which are not toxic or have other disadvantageous effects. Preferably, the at least one soluble calcium salt is selected from calcium citrate, calcium lactate, calcium gluconate, calcium lactate gluconate, calcium lactobionate and mixtures thereof.

The nutritional supplement according to the invention can, as a combination preparation, contain further components which have a positive effect on the health of the bones or are generally useful as a nutritional supplement. It is particularly favourable if, for example, the nutritional supplement also comprises one or more vitamins selected from vitamin C, vitamin D, vitamin $D_3$, vitamin E, vitamin K and the metabolites thereof.

Furthermore, the nutritional supplement according to the invention can also be enhanced with different minerals, for example, fluorine salts, potassium salts and magnesium salts. The uptake of such minerals by means of the intestinal wall can also be promoted by short-chain fatty acids.

A further advantageous addition are omega-3 fatty acids which can lead to an increase of the calcitonin content in the bones. An anti-inflammatory effect is also attributed to them.

Soya isoflavones possibly also have a positive effect on the bone density and can be used in the nutritional supplement according to the invention.

Finally, spices or their active ingredients, for example, curcumin and chilli which, with their anti-inflammatory and immunomodulatory effect, can contribute to the advantageous effects of the nutritional supplements according to the invention are also to be mentioned.

Through the positive effect of the collagen hydrolysate according to the invention on the bone health, its administration as a nutritional supplement may enable, under some circumstances, dispensing with, or at least a dose reduction in, drugs which are otherwise used for this purpose, in particular to prevent and/or treat postmenopausal osteoporosis. Examples of such pharmaceutical active ingredients, the use of which is sometimes not without problems, are selective oestrogen receptor modulators (SERMs), parathormone and its analogue teriparatide, other hormones (in particular oestrogens and growth hormones), biphosphonates and monoclonal antibodies.

A further object of the invention is a method for producing the collagen hydrolysate according to the invention, comprising the steps:
  production of an aqueous solution of type-B bone gelatin with a concentration of 5% to 20% by weight, in particular approximately 10% by weight;
  addition of a neutral endoprotease from *Bacillus subtilis* in a quantity of 1% to 4% by weight, particularly approximately 2% relative to the quantity of gelatin;
  allowing the endoprotease to act on the gelatin at a temperature of 40° C. to 60° C., particularly approximately 50° C., and at a pH value of 5.5 to 6.5, particularly approximately 6, over a period of 20 min to 40 min, particularly approximately 30 min; and
  thermal deactivation of the endoprotease.

Particular advantages and preferred embodiments of the method according to the invention have already been described in conjunction with the collagen hydrolysate according to the invention.

BRIEF DESCRIPTION OF THE SEVERAL VIEWS OF THE DRAWING(S)

Figure 2:
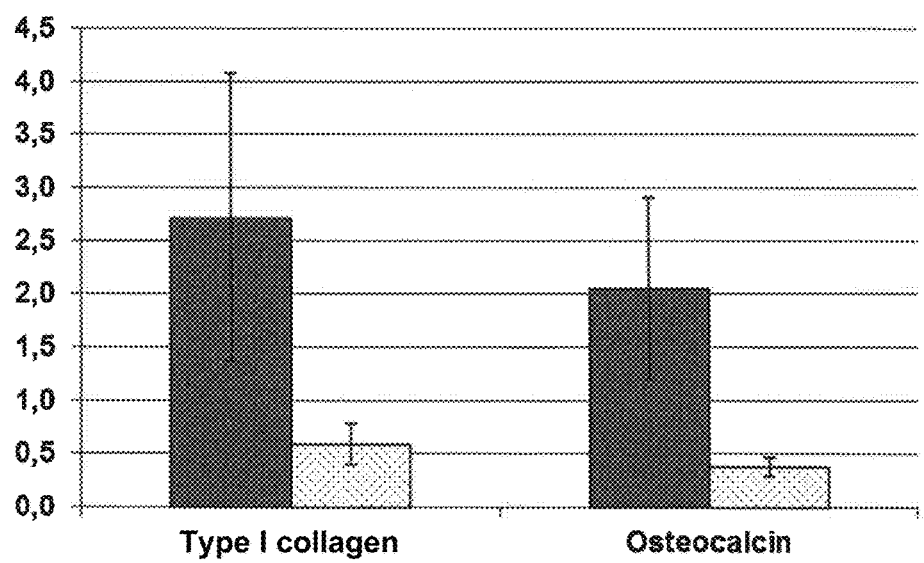

The invention will now be described in greater detail using the following examples and making reference to the Figures, in which:

FIG. 1: shows a gel permeation chromatogram with the molecular weight distribution of a collagen hydrolysate according to the invention and a comparison hydrolysate;

FIG. 2: shows a graphical representation concerning the stimulation of the synthesis of type I collagen and osteocalcin by a collagen hydrolysate according to the invention and a comparison hydrolysate; and FIG. 3: shows a graphical representation concerning the stimulation of the synthesis of different matrix proteins and enzymes by a collagen hydrolysate according to the invention and four different comparison hydrolysates.

PRODUCTION OF COLLAGEN HYDROLYSATES

The production of a collagen hydrolysate according to the present invention (example) and of four collagen hydrolysates not according to the invention (comparative examples 1 to 4) will now be described.

Two different gelatins were used as starting materials, specifically a type-B gelatin from beef bones (identified below as bone gelatin) and a type-A pig skin gelatin. The essential parameters thereof are shown in Table 1.

TABLE 1

| | Bone gelatin | Pig skin gelatin |
|---|---|---|
| Bloom strength | 298 g | 299 g |
| Viscosity (6.67% by weight, 60° C.) | 5.52 mPa · s | 3.90 mPa · s |
| Conductivity (1% by weight, 30° C.) | 111 µS/cm | 157 µS/cm |
| Moisture | 10.7% | 9.6% |
| Isoelectric point | 5.04 | 9.16 |
| Amidation level | 6.7% | 31.7% |

EXAMPLE 200 g bone gelatin was soaked in 1800 g distilled water for 30 min at room temperature. The pre-soaked gelatin was heated to 58±2° C. and dissolved while stirring. The pH value was adjusted with sodium hydroxide solution to 6.0±0.2. A neutral endoprotease from *Bacillus subtilis* in a quantity of 2% by weight (in relation to the gelatin) was then added. After a hydrolysis duration of 30 min, the solution was heated to 85° C. for enzyme deactivation. To obtain the collagen hydrolysate formed, the solution was dried.

Comparative Example 1

200 g bone gelatin was soaked in 1800 g distilled water for 30 min at room temperature. The pre-soaked gelatin was heated to 49±2° C. and dissolved while stirring, following which 1.64 g CaCl$_2$.2H$_2$O was added. The pH value was adjusted with sodium hydroxide solution to 6.0±0.2. Thereafter, 0.6% by weight (in relation to the gelatin) of a neutral endoprotease from *Bacillus subtilis* was added. After a hydrolysis duration of 30 min, 0.2% by weight (in relation to the gelatin) of a neutral endoprotease from *Bacillus amyloliquefaciens* was added. After a total hydrolysis duration of 180 min, the solution was heated to 85° C. for enzyme deactivation and then dried.

The molecular weight distribution of the peptides of the different collagen hydrolysates was determined by means of gel permeation chromatography, using the following parameters:
Static phase: TSK 2000 SW XL (Tosoh Bioscience GmbH)
Mobile phase: 0.4 mol/1 monosodium phosphate pH 5.3
Flow rate: 0.5 ml/min
Calibration standard: defined collagen-type I fragments (FILK, Freiberg)
Detection: UV detector Knauer K-2501 at 214 nm Table 2 contains the respective molecular weight distribution according to the predetermined weight fractions, the mean molecular weight, the viscosity and the pH value (each at 20% by weight and 25° C.) and the amidation level of the different collagen hydrolysates.

TABLE 2

| Fractions | Example | Comparative Example 1 | Comparative Example 2 | Comparative Example 3 | Comparative Example 4 |
|---|---|---|---|---|---|
| >18 kDa | 4.3 | 0.1 | 0 | 0.8 | 0 |
| 13.5-18 kDa | 2.9 | 0.2 | 0.1 | 2.0 | 0 |
| 7.5-13.5 kDa | 21.1 | 5.0 | 0.7 | 20.6 | 0 |
| 3.5-7.5 kDa | 29.8 | 25.4 | 10.6 | 25.8 | 0.9 |
| 1.5-3.5 kDa | 24.5 | 34.6 | 24.3 | 22.8 | 10.9 |
| 0.5-1.5 kDa | 15.1 | 31.0 | 46.4 | 20.5 | 70.9 |
| <0.5 kDa | 2.4 | 3.7 | 18.0 | 7.4 | 17.4 |
| Mean MW | 5,800 Da | 2,900 Da | 1,800 Da | 4,700 Da | 950 Da |
| Viscosity | 6.77 mPa·s | 4.15 mPa·s | 3.22 mPa·s | 5.61 mPa·s | 2.45 mPa·s |
| pH value | 6.2 | 6.1 | 6.4 | 6.0 | 6.5 |
| Amidation level | 6.8% | N/A | N/A | N/A | 27.6% |

Comparative Example 2

200 g bone gelatin was soaked in 1800 g distilled water for 30 min at room temperature. The pre-soaked gelatin was heated to 49±2° C. and dissolved while stirring, following which 0.4 g CaCl$_2$.2H$_2$O was added. The pH value was adjusted with sodium hydroxide solution to 6.5±0.2. Thereafter, 0.6% by weight (in relation to the gelatin) of a neutral endoprotease from *Bacillus subtilis* was added. After a total hydrolysis duration of 60 min, 0.2% by weight (in relation to the gelatin) of an exoprotease from *Aspergillus sojae* was added. After a hydrolysis duration of 7 h, the solution was heated to 85° C. for enzyme deactivation and then dried.

Comparative Example 3

200 g pig skin gelatin was soaked in 1800 g distilled water for 30 min at room temperature. The pre-soaked gelatin was heated to 57±2° C. and dissolved while stirring. The pH value was adjusted with sodium hydroxide solution to 6.0±0.2. Thereafter, 0.3% by weight (in relation to the gelatin) of a neutral endoprotease from *Bacillus subtilis* was added. After 180 min, the solution was heated to 85° C. for enzyme deactivation and then dried.

Comparative Example 4

200 g pig skin gelatin was soaked in 1800 g distilled water for 30 min at room temperature. The pre-soaked gelatin was heated to 58±2° C. and dissolved while stirring. The pH value was adjusted with sodium hydroxide solution to 7.0±0.2. Thereafter, an alkaline endoprotease from *Bacillus licheniformis* in a quantity of 2% by weight (in relation to the gelatin) was added. After 180 min, the solution was heated to 85° C. for enzyme deactivation and then dried.
Determination of the Molecular Weight Distribution FIG. 1 shows the gel permeation chromatogram with the molecular weight distribution of the collagen hydrolysate according to the invention as in the example and the collagen hydrolysate according to comparative example 4. The molecular weight is entered on the abscissa with a logarithmic scale.
Stimulation of the Synthesis of Matrix Proteins and Enzymes In Vitro As evidence of the particular effectiveness of the collagen hydrolysate according to the invention, the stimulating effect thereof on the synthesis of matrix proteins and enzymes which play a part in the building up and mineralisation of the matrix was investigated in vitro by means of osteoblasts. This was carried out by determining the expression of the relevant mRNA by means of real time PCR and a semi-qualitative evaluation (in relation to a control without any collagen hydrolysate).

The human osteoblasts were isolated from knee joints in that bone material was incubated under severe agitation at 37° C. for 1 h in Hanks solution, supplemented with 7 mg/ml of hyaluronidase type I and III-S and 5 mg/ml pronase. The breakdown was then continued at 37° C. in Hanks solution for 3-5 h, supplemented with 16 mg/ml collagenase type CLS IV. Following the enzymatic breakdown, primary osteoblasts were cultivated in HAMs F12 medium, supplemented with 10% foetal calf serum, 20 U/ml penicillin streptomycin, 50 µg/ml patricin, 0.05 mg/ml ascorbic acid and 0.15 mg/ml glutamine.

For the actual investigation, monolayer cell cultures of the human osteoblasts were incubated for a period of 24 h in a medium which had been supplemented with 0.5 mg/ml of the relevant collagen hydrolysate (according to the example or one of the comparative examples). In each case, a control was incubated in a medium without hydrolysate. Subsequently, the determination of the relevant mRNA expression was carried out as described above.

The results for the stimulation of the synthesis of type I collagen and osteocalcin are shown as a histogram in FIG. 2, the left-hand column being the example according to the invention in each case and the right-hand column being comparative example 4 in each case. Represented on the ordinate is the mRNA expression relative to the control (=1) (mean value and standard deviation from at least 12 independent tests). Whereas type I collagen represents by far the most important matrix protein of the bone material, osteocalcin is an enzyme involved in the differentiation of the matrix, the enhanced expression of which also favours the building up of the matrix.

In both cases, there is a significant stimulating effect of the hydrolysate according to the invention, specifically an enhancement of the collagen mRNA expression on average by a factor of approximately 2.7, and the osteocalcin mRNA expression is enhanced on average by a factor of approximately 2.0. Interestingly, as distinct therefrom, the hydrolysate according to comparative example 4, which is produced from a different starting material and has a lower mean molecular weight, actually leads to a reduction in the expression of the two mRNAs, which demonstrates the high specificity of the collagen hydrolysate according to the invention.

Corresponding results for the stimulation of the synthesis of type I collagen, biglycan, versican and alkaline phosphatase are shown as a histogram in FIG. 3, the columns from left to right standing respectively for the example according to the invention and the comparative examples, 1, 2 and 3 (mean value and standard deviation from at least 12 independent tests). Biglycan and versican are proteoglycans which play a part in the structural organisation of the bone matrix. Alkaline phosphatase is—alongside other functions—involved similarly to osteocalcin in the differentiation of the bone matrix.

Here also, it can be seen that, for all four proteins the collagen hydrolysate according to the invention has a better effect than all the comparative examples. Of the latter, only comparative example 3 has a slightly stimulating effect on the synthesis of type I collagen (by a factor of approximately 1.3), whilst in all the other cases, there is no, or even a negative effect, i.e. a reduction in the mRNA synthesis. Although with biglycan, versican and alkaline phosphatase, the effect of the collagen hydrolysate according to the invention is also relatively weak, it is more positive in each case than that of the other hydrolysates.

The improved effectiveness of the collagen hydrolysate according to the invention as compared with various other hydrolysates is therefore confirmed with regard to all the matrix proteins and enzymes investigated, the enhanced expression of which promotes the building up of the bone matrix.

The invention claimed is:

1. A collagen hydrolysate which is produced by enzymatic hydrolysis of type-B bone gelatin, wherein the collagen hydrolysate is formed from hydrolyzed collagen peptides of which at least 50% by weight have a molecular weight of 1,500 Da to 13,500 Da, and which have a weight average molecular weight in the range from 4,000 Da to 8,000 Da, wherein the bone gelatin is produced by alkaline breakdown of collagen from bones of vertebrates.

2. The collagen hydrolysate according to claim 1, wherein the bone gelatin has an isoelectric point of below 5.5.

3. The collagen hydrolysate according to claim 1, wherein the peptides have an overall amidation level of glutamine groups and/or glutamic acid groups and of asparagine groups and/or aspartic acid groups of less than 15%.

4. The collagen hydrolysate according to claim 1, wherein a 20% by weight aqueous solution of the collagen hydrolysate has a viscosity at 25° C. of more than 5 mPa·s.

5. The collagen hydrolysate according to claim 1, wherein the collagen hydrolysate has an ammonium, sulphate and phosphate content of less than 300 ppm each.

6. The collagen hydrolysate according to claim 1, wherein the collagen hydrolysate is produced by hydrolysis of the gelatin with a neutral endoprotease from *Bacillus subtilis*.

7. The collagen hydrolysate according to claim 6, wherein the collagen hydrolysate is produced through the action of the endoprotease at a temperature of 40° C. to 60° C. over a period of 20 min to 40 min.

8. The collagen hydrolysate according to claim 1, wherein the collagen hydrolysate is a nutritional supplement.

9. A nutritional supplement comprising the collagen hydrolysate of claim 1 and one or more prebiotics.

10. The nutritional supplement according to claim 9, wherein the prebiotic or prebiotics is/are selected from oligosaccharides and/or polysaccharides.

11. The nutritional supplement according to claim 9, further comprising one or more soluble calcium salts.

12. The nutritional supplement according to claim 9, further comprising one or more vitamins which are selected from vitamin C, vitamin D, vitamin $D_3$, vitamin E, vitamin K and the metabolites thereof.

13. The nutritional supplement according to claim 9, further comprising one or more minerals which are selected from the group consisting of fluorine salts, potassium salts and magnesium salts.

* * * * *